United States Patent [19]

Lancee et al.

[11] Patent Number: 5,240,003

[45] Date of Patent: Aug. 31, 1993

[54] ULTRASONIC INSTRUMENT WITH A MICRO MOTOR HAVING STATOR COILS ON A FLEXIBLE CIRCUIT BOARD

[75] Inventors: Charles T. Lancee, Waarder; Nicolaas Bom, Berkenwoude, both of Netherlands

[73] Assignee: Du-Med B.V., Rotterdam, Netherlands

[21] Appl. No.: 820,571

[22] Filed: Jan. 14, 1992

Related U.S. Application Data

[63] Continuation-in-part of Ser. No. 765,084, Sep. 24, 1991, abandoned, which is a continuation-in-part of Ser. No. 591,652, Oct. 2, 1990, Pat. No. 5,176,141.

[30] Foreign Application Priority Data

Oct. 16, 1989 [NL] Netherlands ............... 89 02559

[51] Int. Cl.⁵ .................. A61B 8/12; H02K 21/00
[52] U.S. Cl. .................. 128/662.06; 310/40 MM; 310/162
[58] Field of Search .......... 128/660.1, 662.06; 310/40 MM, 156, 162, 184, DIG. 6

[56] References Cited

U.S. PATENT DOCUMENTS

| | | | |
|---|---|---|---|
| 4,645,961 | 2/1987 | Malsky | 310/DIG. 6 X |
| 4,665,331 | 5/1987 | Sudo et al. | 310/DIG. 6 X |
| 4,728,834 | 3/1988 | Kumar et al. | 310/DIG. 6 X |
| 4,962,329 | 10/1990 | Fujita et al. | 310/DIG. 6 X |
| 4,975,607 | 12/1990 | Hara et al. | 310/DIG. 6 X |

OTHER PUBLICATIONS

Bom, N. et al., "Earlyand Recent Intraluminal Ultrasound Devices", Intnl Jrnl of Cardiac Imaging vol. 4 pp. 79–88 1989.

*Primary Examiner*—Francis Jaworski
*Attorney, Agent, or Firm*—Thomas R. Vigil

[57] ABSTRACT

The disposable intra-luminal ultrasonic instrument for the examination and/or treatment of blood vessels and similar lumina has a small transverse cross-section. The instrument includes a catheter comprising a body and a tip having a distal end and a distal portion adapted to be introduced into a lumen and a proximal portion. The catheter has a diameter no greater than 3 millimeters, a rotatable member in the tip, a micro motor in the tip and coupled to the rotatable member for rotating the rotatable member at a selected rpm, the motor having flat stator coils mounted on a flexible circuit board, and means for generating and supplying sound waves to the rotatable member.

38 Claims, 6 Drawing Sheets

ULTRASONIC INSTRUMENT WITH A MICRO MOTOR HAVING STATOR COILS ON A FLEXIBLE CIRCUIT BOARD

CROSS REFERENCE TO RELATED APPLICATIONS

This application is a continuation-in-part of U.S. patent application Ser. No. 07/765,084 filed Sep. 24, 1991 for: ULTRASONIC INSTRUMENT WITH A MICRO MOTOR HAVING STATOR COILS ON A FLEXIBLE CIRCUIT BOARD, now abandoned, which is a continuation-in-part of U.S. patent application Ser. No. 07/591,652 filed Oct. 2, 1990 for: A DISPOSABLE INTRALUMINAL ULTRASONIC INSTRUMENT, now U.S. Pat. No. 5,176,141 issued on Jan. 5, 1993.

BACKGROUND OF THE INVENTION

1. Field of the Invention

The present invention relates to a disposable intraluminal ultrasonic instrument which includes a catheter that has an ultrasonic sound wave transducer therein and a rotatable acoustic mirror for directing the sound waves outwardly into tissue and for receiving echo sounds and directing the echo sounds to the transducer for transmission to a visual display which displays an ultrasound picture of the tissue whereby one can determine the makeup or construction of the tissue, e.g., hard or soft. The present invention also relates to a micro motor used in such an instrument for rotating the acoustic mirror while the transducer provides sound waves to the acoustic mirror, the micro motor including flat stator coils mounted on a flexible circuit board.

2. Description of the Related Art Including Information Disclosed Under 37 CFR Sections 1.97-1.99

Heretofore it has been proposed in Dutch Patent Application No. 87.00632 to provide a catheter having a catheter tip with a rotatable acoustic mirror therein or a rotatable tip having an acoustic mirror therein. A flexible shaft extends from the rotatable acoustic mirror to the proximal end of the catheter where it is driven by a suitable motor situated outside the catheter. A transducer is mounted in the catheter tip opposite the rotatable acoustic mirror. Rotation of the acoustic mirror within the tip or the tip portion having the mirror thereon causes high frequency ultrasonic vibrations or sound waves emitted by the transducer to be emitted in different directions in a rotating path and the echoes of the sound waves are received by the acoustic mirror and thence by the transducer for transmission to a visual display whereby a picture can be created of the space around the catheter tip which may contain tissue or a stenotic buildup in a vessel.

A problem with the instrument having the catheter described above is that the flexible drive shaft is fairly long, i.e., at least as long as the catheter itself. With this arrangement, it is difficult to supply a torsion free rotational force through the flexible drive shaft and to drive such a long flexible drive shaft for extended periods of time without malfunctioning.

As will be described in greater detail below, the present invention provides an intra-luminal ultrasonic instrument which does not have the problem of a long drive shaft by providing a micro motor of very small diameter in the catheter tip for driving a short drive shaft coupled to an acoustic mirror in the catheter tip, the motor having flat stator coils mounted on a flexible circuit board.

It has been suggested in Dutch Patent Application No. 87.00632 to provide a turbine driven by fluid at or near the catheter tip with the turbine having a short drive shaft coupled to the rotatable acoustic mirror.

Heretofore it has been proposed in European Patent Application Publication No. 0 139 574 to provide an endocavity probe having a motor mounted in the distal end of one embodiment of the probe. The motor rotates a mirror which reflects signals emitted by a transducer.

This probe is utilized in examining organs and the like of a body. The probe is somewhat bulky in shape and size, is intended for insertion in body cavities, is not suitable for insertion inside veins and/or arteries and does not teach a motor having stator coils mounted on a flexible circuit board and having a diameter no greater than 3 millimeters mounted in a catheter tip.

In the Sakai German Offenlegungsschrift DE 32 19 118 A1 there is disclosed an endoscope having a metal housing in which is mounted a rotatable mirror and a motor for rotating the mirror. Also, fiber optics are provided for viewing capabilities. This patent publication does not disclose or suggest a catheter tip no greater than 3 millimeters in diameter having a micro motor mounted therein for rotating an acoustic mirror positioned adjacent to a transducer in the catheter tip.

The Eggleton et al. U.S. Pat. No. 4,546,771 discloses an acoustic microscope which has a transducer capable of producing and receiving high frequency acoustical beams and is positioned within a needle. This patent teaches using frequencies of 100 megahertz to 400 megahertz, and preferably frequencies of 500 megahertz or greater. These frequencies do not produce the necessary depth obtained with frequencies under 60 megahertz as utilized in the ultrasonic instrument of the present invention.

This patent teaches the rotation of a rotating member by an arrangement of small electromagnets and permanent magnets attached to a needle. The needle in this patent can only be inserted into tissue for biopsy procedures and is not adapted to be inserted into a blood vessel like the catheter tip of the present invention for evaluating space around the catheter tip and particularly, the tissue or stenotic buildup located around the catheter tip to a sufficient depth.

A number of ultrasonic instruments for the examination and/or treatment of blood vessels have been previously proposed. Examples of these previously proposed instruments are disclosed in the following United States Patents, the disclosures of which are incorporated herein by reference:

| Patentee | U.S. Pat. No. |
| --- | --- |
| Yock | 4,794,931 |
| Pope et al | 4,889,757 |
| Prodian et al | 4,917,097 |
| Yock | 5,000,185 |
| Lum et al | 5,003,238 |
| Passafaro | 5,010,886 |
| Yock et al | 5,029,588 |

A miniature stepper motor for use in timepiece is disclosed in the Knapen et al U.S. Pat. No. 4,908,808 assigned to Kinetron, B. V., The Netherlands.

SUMMARY OF THE INVENTION

According to the present invention, there is provided an ultrasonic instrument for the examination and/or treatment of blood vessels and similar lumina having a small transverse cross-section, said instrument including a catheter comprising a body and a tip having a distal end and a distal portion adapted to be introduced into a lumen and a proximal portion, said catheter holding a diameter no greater than 3 millimeters, a rotatable member in said tip, a micro motor in said tip having flat stator coils mounted on a flexible circuit board which is coiled into a cylinder and a rotor which is coupled to said rotatable member for rotating said rotatable member at a selected rpm, and means for generating and supplying sound waves to said rotatable member.

DESCRIPTION OF THE PREFERRED EMBODIMENT(S)

Figure 1:
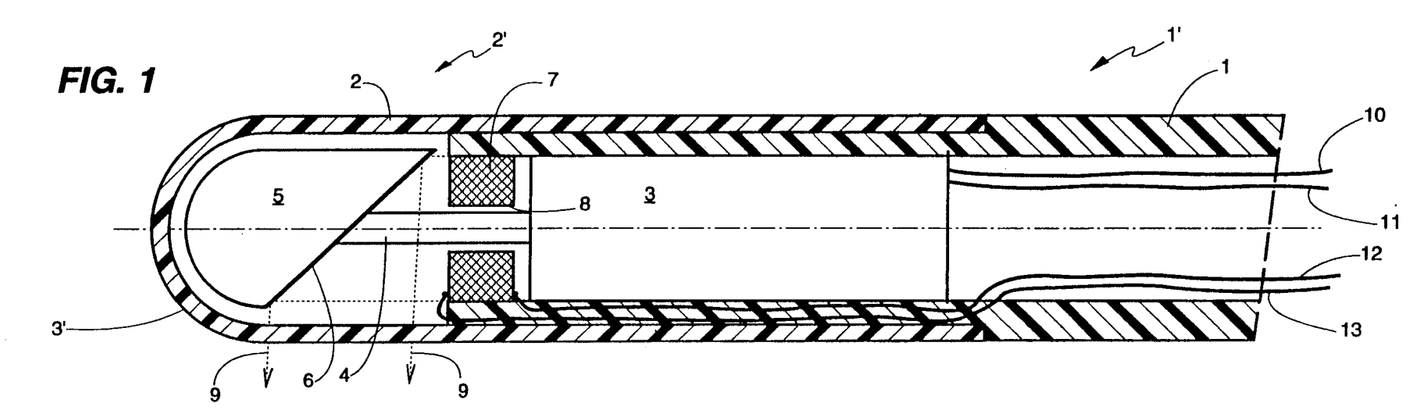
FIG. 1 is a cross-sectional view of a catheter tip of one embodiment of the disposable intra-luminal ultrasonic instrument constructed according to the teachings of the present invention.

Referring now to the Figures in greater detail, there is illustrated in FIG. 1 a catheter in the form of a thin flexible tube made of a suitable disposable material, e.g., a plastic material which forms part of a disposable intra-luminal ultrasonic instrument 1'. The outer diameter of the tube 1 is not more than 2.7 millimeters and will be 0.62 millimeters, if the instrument is used for the examination and/or treatment of coronary vessels.

A small cap 2 of a suitable material, e.g., a plastic material, is fastened onto a distal end portion of the flexible tube 1 to define a catheter tip 2'. The cap 2 is made of a material which is transparent to ultrasonic radiation or sound waves when the instrument is provided with means for emitting ultrasonic radiation and for receiving the echoes of the emitted radiation. In any event, the cap 2 has a window for allowing this ultrasonic radiation to pass through the cap 2.

A cylindrical micro motor 3 is fastened in the distal end portion of the flexible tube 1 near the distal end of the tube 1 with the motor 3 being substantially co-axial with the axis of the catheter tube 1.

In this embodiment of the instrument 1', the motor 3 is placed at some distance from the distal end of the catheter tip 2'.

A drive shaft 4 extends distally from, is part of, and is driven by a motor 3.

A rotatable element, which in this embodiment of the instrument 1' is a rotatable acoustic mirror 5, is mounted on the drive shaft 4 and has a mirror face 6 which lies in a plane that intersects the axis of the catheter tube 1 at an angle, as well as intersecting the axis of the drive shaft 4 of the motor 5. The mirror 5 is rotatable with and on the drive shaft 4 during operation of the motor 3.

The motor 3 can be driven at an rpm between 600 and 4,000 rpm, e.g., 1,200 rpm, 1,800 rpm, 3,000 rpm or 3,600 rpm up to but not limited to 6,000 rpm.

The rotational speed of the motor is correlated with a raster across a visual display (not shown) which is connected to the instrument 1'.

A transducer 7 is mounted within the distal end portion of the catheter tube 1 between the motor 3 and the mirror face 6 opposite or facing the mirror 6.

As shown, the transducer 7 has a central passageway or channel 8 therethrough through which the drive shaft 4 extends.

Ultrasonic radiation at critically selected frequencies is emitted by the transducer 7 at the mirror face 6 and reflected outwardly by the mirror face 6 in the direction generally driven by the arrows 9. This reflected bundle of radiation waves 9 emerges from the catheter tip 2' via a window formed in or defined by the cap 2.

If the ultrasound wave is reflected by an obstacle, such as an artery wall, when the catheter tip is mounted in an artery, the reflected or echoed signal so generated will pass through the window, impinge upon the mirror face 6 and will be reflected to and received by the transducer 7. The reflected sound waves are then supplied by the transducer 7 to a visual display where an ultrasound image of the space surrounding the catheter tip 2' and the material in that space can be displayed on a visual display, the raster of which is coordinated with the speed of rotation of the acoustic mirror 5. The operating frequency of the sound wave will determine the depth of field of this ultrasonic imaging.

It has been found that in the megahertz frequency range lower frequencies, e.g., below 10 megahertz, will provide a deeper depth of field but with low resolution which might not be satisfactory. On the other hand, it has been found that frequencies between 45 and 60 megahertz, while providing good resolution, result in a shallower depth of field. Accordingly, in the instrument 1' of the present invention the ultrasonic sound waves generated by the transducer 7 are generated by a frequency that is not greater than 60 megahertz typically in the range of 15 and 45 megahertz, and preferably at approximately 30 megahertz for a good balance between depth of field and resolution.

The manner in which ultrasonic pictures can be formed of the space surrounding the catheter tip 2' with the aid of echoes or ultrasonic radiation is described in Dutch Patent Application No. 87.00632, the disclosure of which is incorporated herein by reference.

The motor 3 is preferably a synchronous motor. The power supply for the motor 3 can be outside the catheter tube 1 with the motor 3 being coupled to the power supply by a plurality of electrical wire conductors 10 and 11. These wire conductors 10 and 11 extend through the interior of the catheter tube 1 between the power supply and the motor 3 to which they are connected. The wire conductors 10 can be a plurality of current supply wires 10 and the wire conductors 11 can be a plurality of current removal, ground or common, wires 11.

Also, electrical wire conductors 12 and 13 for transmitting the electrical signals to and from the transducer 7 are received within and extend within catheter tube 1 between the transducer 7 on the distal end of the wire conductors 12 and 13 to an external drive and visual drive at the proximal drive of the wire conductors 12 and 13.

Figure 2:
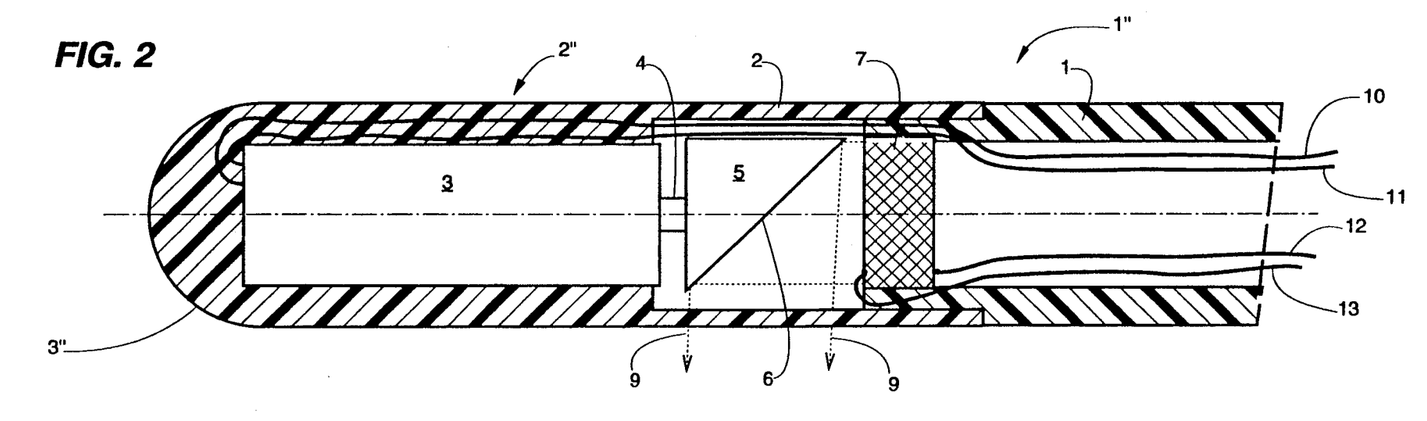
FIG. 2 is a cross-sectional view of a catheter tip, similar to the view shown in FIG. 1, of another disposable intra-luminal ultrasonic instrument constructed according to the teachings of the present invention.

In the embodiment of the disposable ultra-luminal ultrasonic instrument 1", shown in FIG. 2, the motor 3 is mounted in the outer distal end portion 3" of the cap 2. In this embodiment, the drive shaft 4 extends proximally from the motor 3 and has the mirror 5 with mirror face 6 mounted thereon. The transducer 7 is then mounted proximally of the mirror 5 opposite or facing the mirror face 6 within the flexible catheter tube 1 at the distal end thereof.

It will be appreciated that the end cap 2 and motor 3 can be constructed as an integral unit and then mounted on the distal end of the flexible catheter tube 1 with the peripheral area of the cap 2 surrounding the mirror face 6 being of reduced thickness to enable the bundle of ultrasonic waves 9 reflected by the mirror face 6 to pass through the thin wall of the cap 2 and then permit reflected sound waves or echoes to come back through the thin wall of the cap 2. The electrical wire conductors 10 and 11 for the motor 3 and the electrical wire conductors 12 and 13 for the transducer 7 again extend through the interior of the catheter tube 1, as in the embodiment of the instrument 1'shown in FIG. 1.

Figure 3:
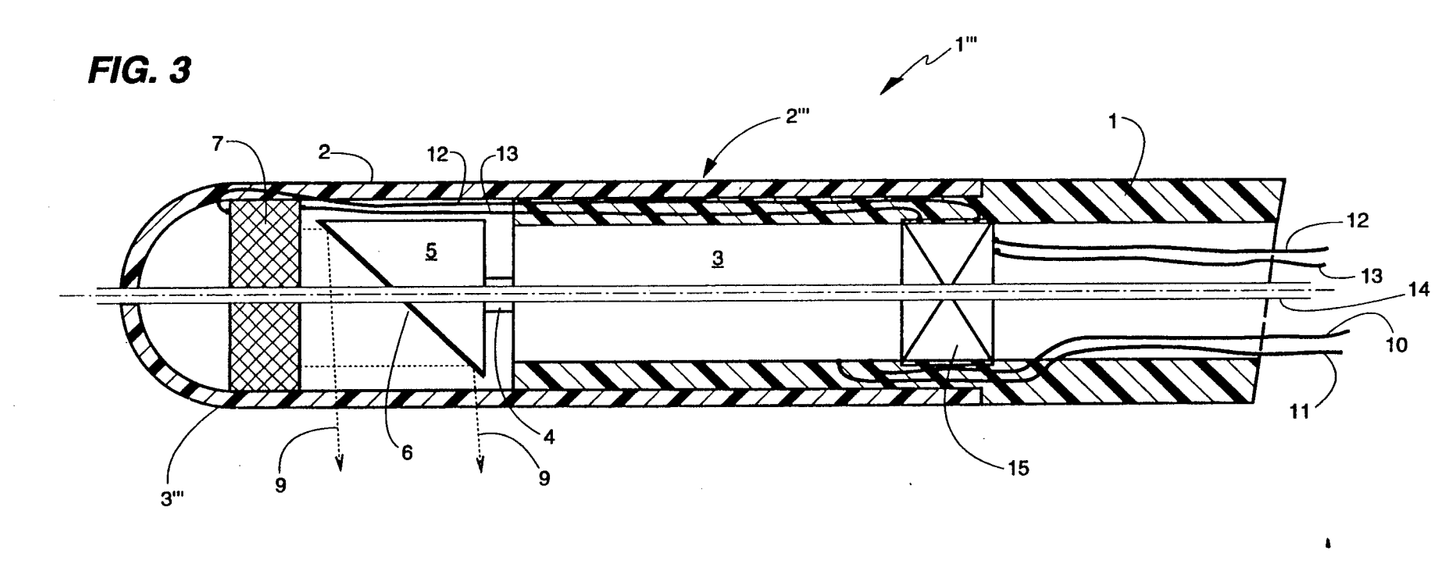
FIG. 3 is a cross-sectional view of a catheter tip, similar to the view shown in FIG. 1, of still another disposable intra-luminal ultrasonic instrument constructed according to the teachings of the present invention.

Referring now to FIG. 3, there is illustrated therein still another embodiment 1''' of the disposable intraluminal ultrasonic instrument of the present invention. In this embodiment, the instrument 1'''has the transducer 7 mounted in a distal end portion 3''' of the cap 2. The motor 3 is then mounted in the distal end portion of the catheter tube 1 much the same way as in the embodiment of the instrument 1' in FIG. 1. Then, the mirror 5 with a mirror face 6, similar to the mirror 5 shown in FIG. 2, is mounted between the transducer 7 and the motor 3 with the mirror face 6 facing the transducer 7 and the acoustic mirror 5 mounted on the drive shaft 4 of the motor 3.

Thus, in FIGS. 1 and 2, the mirror face 6 faces proximally of the catheter tip 2", and in FIG. 3 the mirror face 6 faces distally of the catheter tip 2'''.

Also, in the instrument 1''' shown in FIG. 3, a capillary tube 14 extends through suitable aligned bores in the motor 3, the drive shaft 4, the mirror 5, the transducer 7 and the distal end of the distal end portion 3''' of the cap 2.

With this construction of the instrument 1''', a guidewire can be inserted through the catheter tube 1, namely through the capillary tube 14 and protrude beyond the distal end of the distal end portion 3''' of the cap 2 for various known catheter procedures.

If desired, an electronics switch 15, such as an integrated circuit switch, which includes circuitry for amplifying the reflected or echoed signal received by the transducer 7 before such signal is transmitted via the wire conductors 12 and 13 to the visual display, can be provided.

Furthermore, the wire conductors 10 and 11 to the motor 3 and/or the wire conductors 12 and 13 to the transducer 7 can be used jointly as means for determining the position of a catheter in a lumen, i.e., to determine the relative position of a catheter tip 2 with respect to the surrounding space.

In the instrument 1' shown in FIG. 1, the wire conductors 12 and 13 extend from the transducer 7 through, or are embedded in, the distal end portion of the catheter tube 1 and the wire conductors 10 and 11 extend proximally from the motor 3.

In the instrument 1" shown in FIG. 2, the wire conductors 10 and 11 are fixed in place in the distal end portion 3" of the catheter tip 2 and extend across or intersect the path of the emitted and reflected sound waves 9 and then through the distal end portion of the catheter tip portion 1 to the interior of the catheter tube 1. Thus, the portion of the wire conductors 10 and 11 in the vicinity of the mirror 5 will be seen on the visual display so that the position of the catheter tip relative to the area of the lumen or blood vessel under investigation can be determined.

Likewise, the position of a portion of the wires 12 and 13 extending within the cap 2 in the vicinity of the mirror 5 can be seen on the visual display for determining the orientation and location of the catheter tip 2" relative to the area of the lumen or blood vessel under investigation.

This orientation method is comparable to the orientation method described in Dutch Patent Application No. 89.01084, the disclosure of which is incorporated herein by reference.

From the foregoing description of the embodiments 1', 1". 1''' shown in FIGS. 1-3, the positions, respectively, of the motor 3, the mirror 5 and the transducer 7 can be adjusted as desired.

The mirror face 6 is angled to the catheter axis in a manner as taught in Dutch Patent Application No. 87.00632.

In the embodiment shown in FIG. 1, the transducer 7 has a central channel 8 through which the drive shaft 4 can extend.

The motor 3 of the intra-luminal ultrasonic instrument 1', 1" or 1''' is substantially cylindrical and has a length of less than approximately 6 millimeters, and a diameter of not more than approximately 2.4 millimeters, preferably not more than approximately 1 millimeter.

Also, as described above, devices such as the electrical wire conductors and their position can be utilized for determining the orientation of the catheter tip with respect to the surrounding space as taught in Dutch Patent Application No. 89.01084.

The instrument 1', 1" or 1'" can be fitted in a suitable manner with devices to perform an examination inside the artery or vein after the examination has taken place, or even during the examination, to use an obstructive method, for example, for destroying plaque.

The instrument 1', 1" or 1'" can, for example, be fitted with devices to perform the spark erosion method, as described in the Dutch Patent Application No. 87.00632.

It is also possible to provide the instrument 1', 1" or 1'" with a balloon for use in a balloon dilatation method which is well known in the field of angioplasty. In the practice of an angioplasty method a suitable balloon can be fastened around the catheter tip 2', 2", 2'", and a separate channel can be built in along the catheter tube 1 which is connected to the balloon for inflating it while operating it and thereafter allowing the balloon to deflate.

As described in connection with the description of FIG. 3, a central channel or capillary tube 14 can be provided for receiving a guidewire through the catheter tube 1 and the catheter tip 2'".

The space in the catheter tip 2', 2" or 2'" where the transducer 7 and mirror tip 5 are located is primarily filled with a liquid before operating the instrument 1', 1" or 1'" to ensure efficient acoustical operation of the instrument 1', 1" or 1'". The above referred to space can be pre-evacuated using vacuum techniques and liquid can be sucked into the space via suitable channels. It is also possible to directly introduce liquid into the space via a filling tube so that the air or other gas present is expelled via suitable degassing channels in the catheter tube 1. The filling tube can be a separate lumen in the catheter tube 1 or can be a small tube fitted along or in the catheter tube 1 itself and which can be pulled away after use.

Furthermore, if desired, the integrated switch 15, as shown in FIG. 3, can be mounted in the catheter tip 2" of the instrument 1', 1" or 1'" adjacent the motor 3 and the transducer 7. This structural arrangement can be provided to assist the amplification of the echo signal emitted by the transducer 7 before it is transmitted by the wire conductors 12 and 13 to the visual display; and such amplification allows certain structure in or on the catheter tube 1 to be omitted, e.g., the provision of a metal wire integrated with the catheter mantle, and working as a Faraday's cage, and concealed within the catheter tube 1 can be omitted.

The instrument 1', 1" or 1'" works well with a French 5 catheter having a diameter of approximately 1.6 millimeters.

Furthermore, the transducer 7 is constructed, arranged and operated to emit sound waves at no more than 60 megahertz, typically somewhere between 15 and 45 megahertz, and in one preferred use of the instrument 1', 1" or 1'", at approximately 30 megahertz.

It has been found that the frequencies used, particularly approximately 30 megahertz, results in an ultrasound picture having a depth of field of at least one-half inch ($\frac{1}{2}$") with good resolution so that the makeup or constitution, e.g., hard calcified or soft fatting material, of the tissue or stenotic buildup being investigated can be determined. Furthermore, the instruments 1', 1" or 1'" having the constructions described above with reference to FIGS. 1-3, are constructed in a simple and inexpensive manner which allows the instrument 1', 1" or 1'" to be a disposable instrument.

Figure 4:
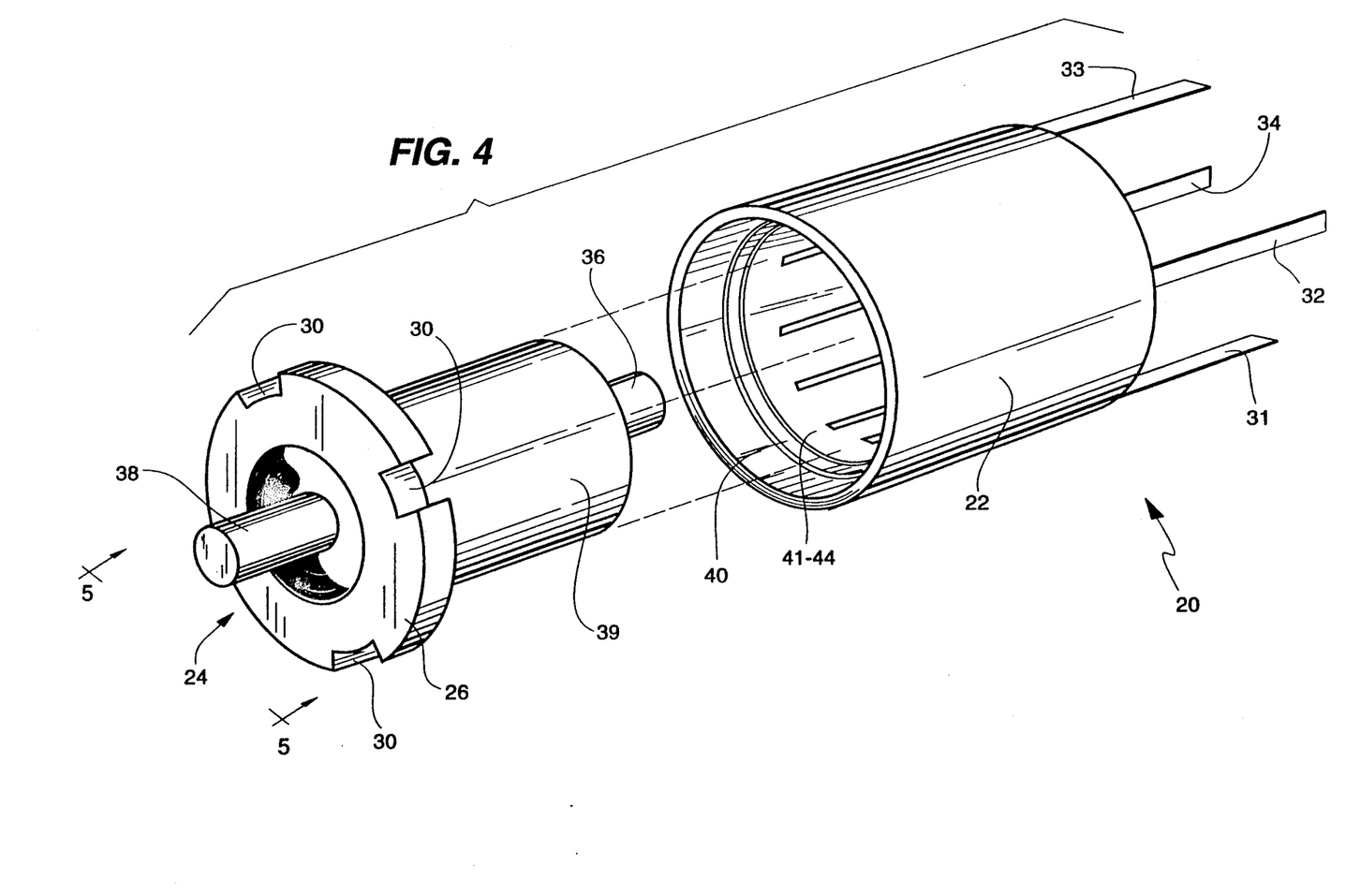
FIG. 4 is an exploded perspective view of a micro motor constructed according to the teachings of the present invention and having flat stator coils mounted on a flexible circuit board which is folded to a cylindrical shape.
Figure 5:
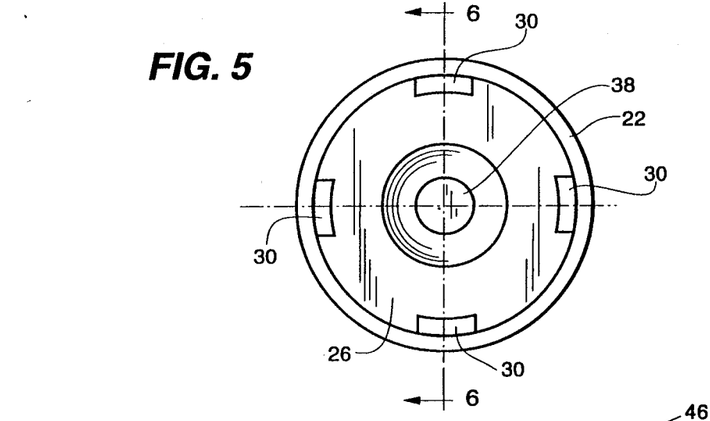
FIG. 5 is an end view of the micro motor showing the output shaft end of the motor.
Figure 6:
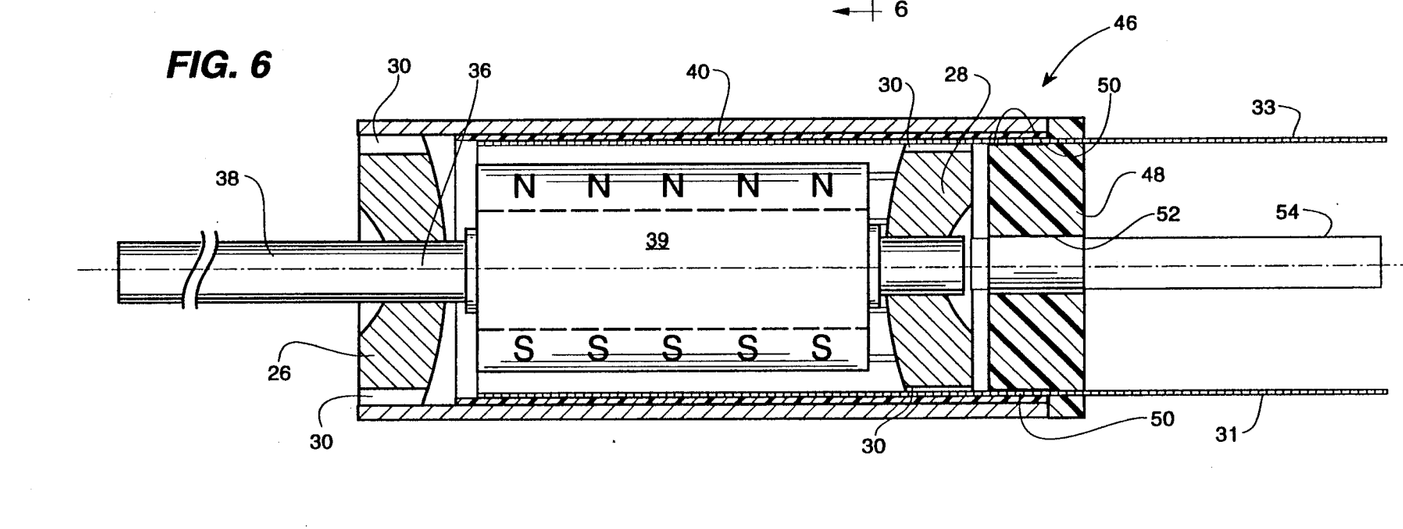
FIG. 6 is a longitudinal sectional view of the micro motor and is taken along line 6—6 of FIG. 5.

In FIGS. 4-6 there is illustrated a micro motor 20 that is a flex print micro motor 20 particularly adapted for use in the intra-luminal ultrasonic instrument 1, 1', 1" or 1'" shown in FIGS. 1-3. As shown in FIGS. 4-6, the flex print micro motor 20 includes a non-magnetic stator shell or housing 22. Mounted at one end, and typically the distal end 24 of the motor 20, is a first bearing 26 and within the stator housing 22 is mounted a similar second bearing 28 (FIG. 6). Each of the bearings 26 and 28 has four side holes or notches 30 equidistantly spaced around the bearing 26, 28 to provide for passage of fluid through the bearing 26 or 28 and then through the motor 20 and also to provide passage means for stator coil leads 31, 32, 33 and 34. A stainless steel rotor shaft 36 is mounted in and between the bearings 26 and 28 with a distal end portion 38 of the shaft 36 extending outwardly from the motor 20. A rotor 39 of the motor 20 has permanent magnets N and S, mounted thereon having opposite pluralities to provide a two pole rotor 39, as shown in FIG. 6.

Figure 7:
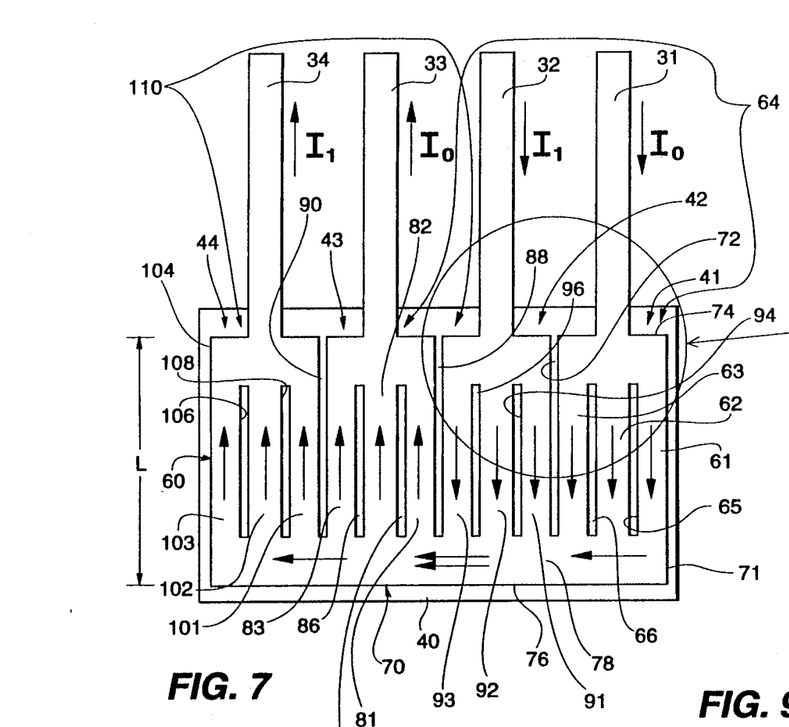
FIG. 7 is a plan view of the flexible circuit board with the flat frame stator coils mounted thereon before it is folded into a cylindrical shape, as shown in FIG. 4.

According to the teachings of the present invention, mounted adjacent the inner surface of the stator housing 22 is a flexible circuit board 40 having mounted thereon four flat stator coil branches 41, 42, 43 and 44 (FIG. 7). The geometry of the stator coil branches 41-44 printed on the flexible circuit board 40 converts a two phase alternating current into a rotating sinusoidal current distribution thereby providing the necessary constant rotation and lower power dissipation required for the motor 20.

At what is typically the proximal end 46 of the motor 20 there is mounted an end cap 48 having slots 50 therethrough through which the leads 31, 32, 33 and 34 can extend and a central passageway 52 therethrough which receives a tube 54 for supplying or withdrawing fluid from inside the motor 20 as shown in FIG. 6. Such fluid can flow through the passageway 52 in the end cap 48, the notches 30 in one bearing 28, around the rotor 39 and through the notches 30 in the other bearing 26 when it is desired to deliver fluid to the vessel in which the motor 20 is located.

Alternatively, fluid can be withdrawn from the vessel via these passages to the tube 54 when, for example, a vacuum is placed on the tube 54.

Referring now to FIG. 7 it will be seen that the stator coil branches 41, 42, 43 and 44 are integral with each other in one stator coil formation 60 with a first input lead 31 leading to three legs 61, 62 and 63 of the coil branch 41 of a first frame coil 64, the legs 61-63 being defined between internal notches 65 and 66 which are etched or otherwise formed through a sheet 70 of conductive, e.g., metal or metallic, material from which the coil formation 60 is formed and by a side edge 71 of the sheet 70 and a slot 72 extending from an upper edge 74 of the sheet 70 from which the leads 31-34 extend toward a lower edge 76, but only to a lower margin 78.

The circuit board is made of Kapton TM and has a thickness of between 0.01 and 0.03 millimeters (mm). The sheet of conductive material is preferably made of copper and has a thickness between 0.01 and 0.03 mm.

Figure 8:
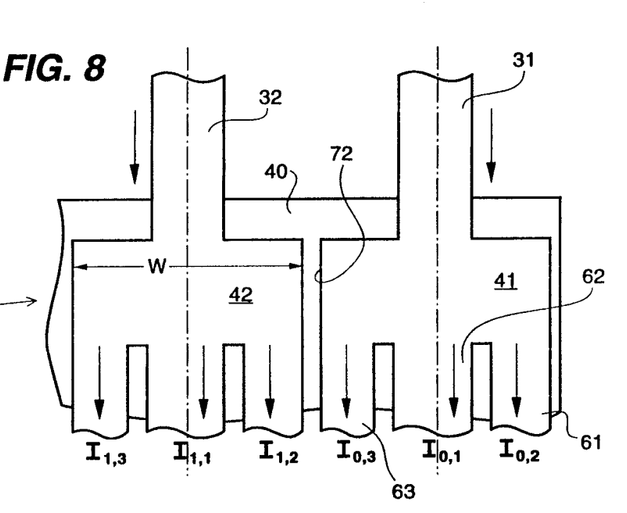
FIG. 8 is an enlarged fragmentary view, with portions broken away, of a portion of the circuit board and flat stator frame coils thereon shown in FIG. 7.

The preferred approximate dimensions of the coils and leads are as follows:

Coil lead length: between 1.0 and 10.0 mm.
Coil lead width: between 0.1 and 0.5 mm.
Coil legs width: between 0.02 and 10.0 mm.
Coil width, W (FIG. 7): between 0.5 and 10.0 mm.
Coil length, L (FIG. 8): between 0.1 and 10.0 mm.
Coil formation length: between 0.5 and 50.0 mm.
Coil formation thickness: between 0.02 and 2.0 mm.
Slots and notches width: between 0.02 and 5.0 mm.
Notch length: between 0.1 and 10.0 mm.
Slot length: between 0.1 and 10.0 mm.

In one preferred embodiment, the leads are approximately 0.20 mm wide and approximately 1.70 mm long. The coils are approximately 0.625 mm wide and approximately 1.50 mm long. The slots and notches are approximately 0.050 mm wide. The first and third legs of each coil branch are approximately 0.154 mm wide with the second or middle leg being approximately 0.217 mm. The coil formation 60 has a length of approximately 2.65 mm. The circuit board is approximately 0.015 mm thick and the sheet of conductive material is approximately 0.015 mm thick.

A current $I_0$ flows into the lead 31 through the legs 61-63 of the first coil branch 41 and in and along the lower margin 78 of the coil formation 60 to the third coil branch 43 which is interconnected by the margin 78 to the first coil branch 41 to form the first frame coil 64. The third coil branch 43 is formed with three legs 81, 82 and 83 between two internal notches 84 and 86 and another two slots 88 and 90 which separate the second coil branch 42 from the third coil branch 43 and the third coil branch 43 from the fourth coil branch 44. The three leg coil branch 43 is disposed opposite the first three leg coil branch 41 to form the frame coil 64 when the coil formation 60 is folded into a cylinder.

In like manner, a current $I_1$ goes into the second lead 32 to the second coil branch 42 and through three legs 91, 92 and 93 which are formed between two internal notches 94 and 96 and the slots 72 and 88 which extend to the margin 78. The current $I_1$ will then flow through the margin 78 to the fourth coil branch 44 and then flow through three legs 101, 102 and 103 formed between a side edge 104 of the coil formation 60, the slot 90 and two internal notches 106 and 108 to the lead 34. The second coil branch 42 and the fourth coil branch 44 form a second frame coil 110 which is displaced 90 from the frame coil 64.

Figure 9:
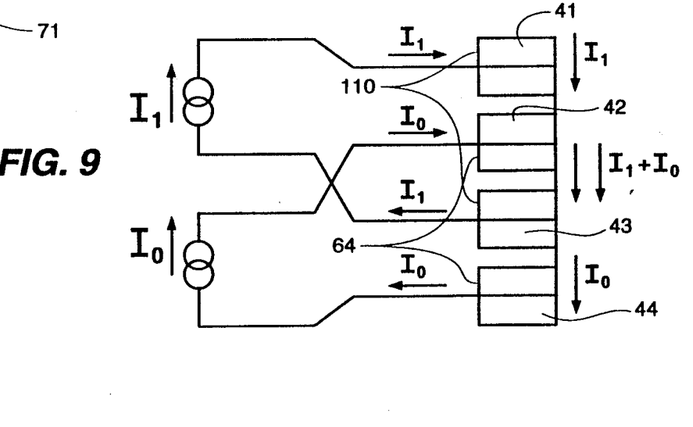
FIG. 9 is an equivalent circuit diagram of the electrical circuit of the stator coils shown in FIG. 7.

The flow of the currents $I_0$ and $I_1$ is shown in more detail in FIGS. 8 and 9.

The current density is approximated to a sinusoidal distribution by splitting the two phase currents into three components, namely $I_{0,1}$ plus $I_{0,2}$ plus $I_{0,3}$ and $I_{1,1}$ plus $I_{1,2}$ plug $I_{1,3}$ as shown in FIG. 8.

In FIG. 9 there is illustrated an equivalent circuit diagram of the stator coil circuits with two current generators $I_1$ and $I_0$. Here the flow of the current $I_1$ and $I_0$ through the stator branch coil 41, 42, 43 and 44 is shown.

The design of the catheter-mounted micro motor 20 and the construction and operation of the frame coils 64 and 110 provide a very small motor without brushes and of minimal complexity which is ideal for the space limitations in blood vessels.

The first and second frame coils combined yields a 2-pole, 2-phase synchronous motor with a permanent magnetic rotor.

Because of the extremely small dimensions involved, the rotor 39 is preferably a composite magnet (an imbedded polymer sold by the company Kinetron at Tilburg, The Netherlands).

The synchronous motor principle requires for two magnetic poles and a set of two frame coil pairs where each coil produces a current density profile of a sinusoidal nature along the circumference.

This is achieved with the frame coils 64 and 110 where, in each frame coil, the number of conductors along the circumference varies as a sinus function.

By using a flexprint design, it is possible to achieve a sinusoidal current density by the use of standard size conductors by varying the pitch. This yields a discrete approximation of the sinus curve.

Due to the limited diameter of the small micro motors, a single-layer flexprint is the preferred construction since it requires an overall thickness of 15 $\mu$m Cu + 15 $\mu$m Kapton ™. This requires each coil branch to extend only over $\frac{1}{4}$ of the circumference.

The sinus curve now has to be approximated over the angle range of $\frac{1}{4}\pi$ to $\frac{3}{4}\pi$ instead of 0 to $\pi$. The contribution of the areas $0 - \frac{1}{4}\pi$ and $\frac{3}{4}\pi - \pi$ is minimal.

Using the total area yields:

$$\int_0^\pi \sin x\, dx = 2$$

or for power leaving out the areas $0 - \frac{1}{4}\pi$ and $\frac{3}{4}\pi - \pi$ yields:

$$\int_0^\pi \sin^2 x\, dx = \frac{1}{2}\pi$$

$$\int_{\frac{1}{4}\pi}^{\frac{3}{4}\pi} \sin x\, dx = \sqrt{2}$$

or for power $$\int_{\frac{1}{4}\pi}^{\frac{3}{4}\pi} \sin^2 x\, dx = \frac{1}{4}\pi + \frac{1}{2}$$

1. Using the total area yields:

$$\int_0^\pi \sin x\, dx = 2[100\%]$$

2. Using one quadrant yields:

$$\int_{\frac{1}{4}\pi}^{\frac{3}{4}\pi} \sin x\, dx = 1.41[71\%]$$

3. Considering power as in 1. yields:

$$\int_0^\pi \sin^2 x\, dx = 1.57[100\%]$$

4. Using one quadrant as in 1. yields:

$$\int_{\frac{1}{4}\pi}^{\frac{3}{4}\pi} \sin^2 x\, dx = 1.29 [82\%]$$

These considerations of power and current density lead to the design of the coil branches 41-44 with the central conductor or middle leg 62, 92, 82 and 102 of each coil branch 41-44 being given a value of 100% current density and the side conductors or side legs 61, 63, 91, 93, 81, 83, 101, and 103 then being 71% ($\frac{1}{2}\sqrt{2}$) of the current density in the middle leg.

It will be appreciated that it is difficult to provide true frame coils with the single-layer printed circuit since the crossing of conductors is not possible. Furthermore a wire bridge would be too bulky and very hard to implement.

For this reason, the separate coil branches 41-44 are all interconnected at one side. This can only work if the sum of all incoming currents is zero. Hence a balanced current source must be used for each of the two phases.

Figure 10:
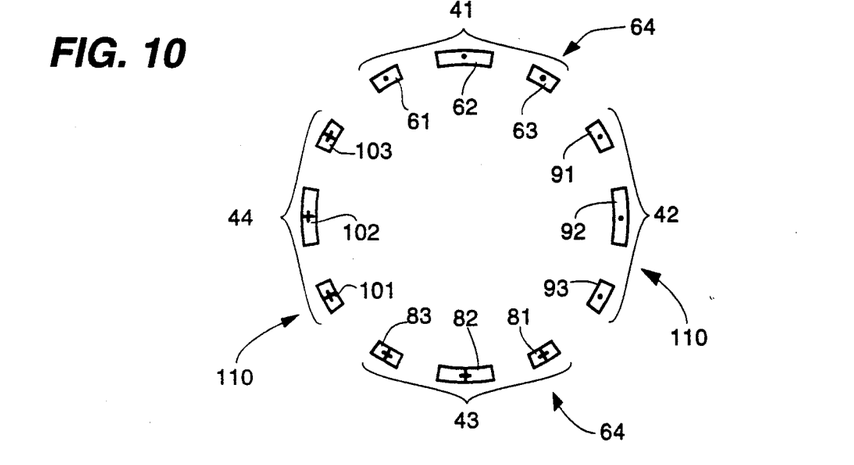
FIG. 10 is a mechanical schematic diagram of a cross-section of the two coil stator frame coils each including first and second branches with each branch having three legs one with the dots representing the current going in at the beginning of a first sinusoidal A.C. current entering the first branch of a first frame coil and of a second sinusoidal A.C. current entering the first branch of a second frame coil and the pluses indicating the first current coming out of the second branch of the first frame coil and the second current coming out of the second branch of the second frame coil.

FIG. 10 shows the arrangement of the coil branches 41 and 43 to form the frame coil 64 and the arrangement of the coil branches 42 and 44 to form the second frame coil 110. Also, there is shown the direction of the current flowing through the coil branches 41-44 at the beginning of the application of the two phases of current which are 90° out of phase from each other.

Figure 11:
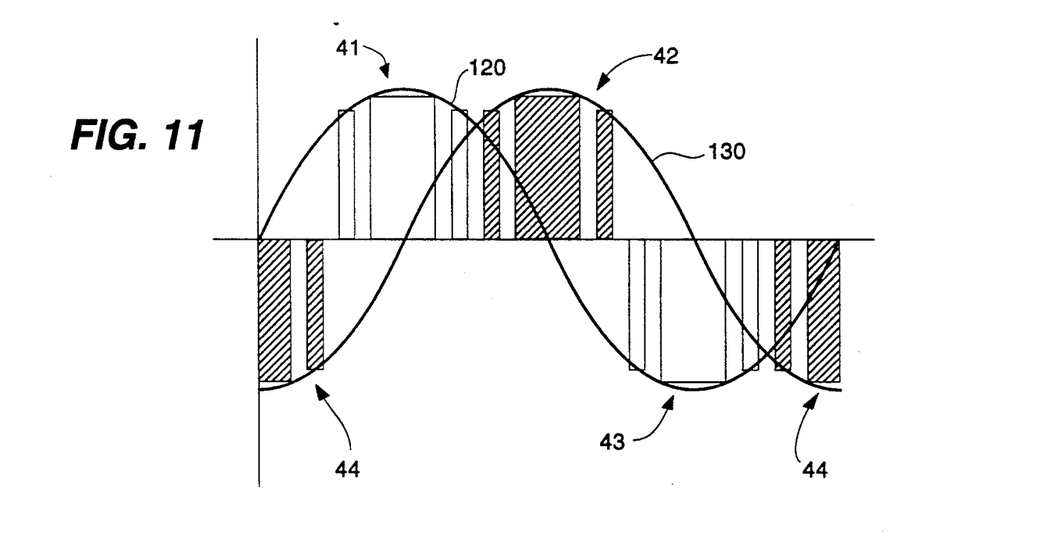
FIG. 11 is a graph of the two phase sinusoidal current waves that are supplied to the two frame coils and through the two branches of each coil with the first phase entering the first branch of the first coil and then exiting out of the second branch of the first coil and the second phase entering the first branch of the second coil and exiting the second branch of the second coil and shows the mechanical effect of the configuration of the branches of the coils affecting the current density such that the effective current density from the three legs of each branch of each coil is represented by rectangles in FIG. 11.

Then, in FIG. 11 there is illustrated the application of the sinusoidal two phase currents 120 and 130 with the phase current 130 being 90° out of phase from the phase current 120. The current density in the motor, as a result of these two sinusoidal currents 120 and 130, out of phase by 90°, as affected by the mechanical construction and arrangement of the coil branches 41-44, and particularly the legs thereof, results in effective current densities in the form of pulses of current through each leg of each coil branch 41-44 of the two frame coils 64 and 110, as shown by the rectangles in FIG. 11.

The combined effect of these effective coil densities (the rectangles in FIG. 11) is a generally sinusoidal, almost square, wave of electromagnetic force. This generally sinusoidal wave of electromagnetic force has few harmonics when compared to ideal two phase motors and, in particular, less second harmonics. Furthermore, as demonstrated by the formulas set forth above, a very high power output of 82% is obtained with the micro motor 20 of the present invention having stator coil branches 41-44 for two frame coils 64 and 110 formed on a printed circuit board.

From the foregoing description it will be apparent that the instrument 1', 1" or 1''' and the micro motor 20 of the present invention have a number of advantages, some of which have been described above and others of which are inherent in the invention. Accordingly, the scope of the invention is only to be limited as necessitated by the accompanying claims.

We claim:

1. An ultrasonic instrument for the examination and/or treatment of blood vessels and similar lumina having a small transverse cross-section, said instrument including a catheter comprising a body and a tip having a distal end and a distal end portion adapted to be introduced into a lumen and a proximal portion, said catheter having a diameter not greater than 3 millimeters, a rotatable member in said tip, and a micro motor in said tip including flat stator coils mounted on at least one flexible circuit board which is coiled into a cylinder, and a rotor which is coupled to said rotatable member for rotating said rotatable member at a selected rpm, and means for generating and supplying sound waves to said rotatable member.

2. The instrument of claim 1 wherein said motor has a side which faces toward said distal end and includes a drive shaft which extends from said side facing said distal end, said rotatable member is a rotatable acoustic mirror which is located in said distal end portion and is connected to said drive shaft, and said rotatable mirror has a mirror face that lies in a plane that intersects at an angle the axis of the drive shaft and the axis of the propagation of sound waves from said means for generating sound waves.

3. The instrument of claim 2 wherein said means for generating sound waves comprises a transducer mounted in said tip between said rotatable member and said motor and has a central passageway therethrough through which said drive shaft extends.

4. The instrument of claim 1 wherein said motor is mounted in said distal end portion and includes a drive shaft extending proximally from said distal end, said rotatable member comprises a rotatable acoustic mirror which is mounted to said drive shaft, said acoustic mirror has a face which lies in a plane which intersects at an angle the axis of said drive shaft and the axis of said propagation of sound waves from said means for generating sound waves and said means for generating sound waves is positioned in said tip opposite said mirror face, which faces proximally from said distal end of said catheter tip.

5. The instrument of claim 1 wherein said motor is generally cylindrical in shape and has a length no greater than approximately 6 millimeters and a diameter no greater than approximately 2.4 millimeters.

6. The instrument of claim 5 wherein said motor has a length no greater than approximately 4 millimeters and a diameter no greater than approximately 1 millimeter.

7. The instrument of claim 1 wherein said motor is operated at a speed of rotation synchronized with a raster across a visual display to which the echoes of the sound waves received by the mirror are supplied and the rotation of the acoustic mirror is oriented with respect to the raster.

8. The instrument of claim 1 wherein said catheter includes electrical conductors for supplying electric power to said motor and to said sound wave generating means.

9. The instrument of claim 1 wherein said catheter has a central channel that also extends through said sound wave generating means and said shaft through and to said distal end of said tip distal portion for receiving a guidewire.

10. The instrument of claim 1 wherein said means for generating sound waves are constructed and arranged to generate sound waves at a frequency no greater than 60 megahertz.

11. The instrument of claim 1 wherein said means for generating sound waves are constructed and arranged to generate sound waves at a frequency of between approximately 15 and 45 megahertz.

12. The instrument of claim 1 wherein said means for generating sound waves are constructed and arranged to generate sound waves at a frequency of approximately 30 megahertz to obtain a sufficient depth of field with sufficient resolution to determine the makeup or constitution of the matter, such as tissue or plaque, in the space being investigated around the catheter tip.

13. The instrument of claim 1 being constructed to be a disposable intra-luminal instrument.

14. The instrument of claim 1 wherein said micro motor is a synchronous two phase alternating current motor having four flat stator coil branches forming two frame coils and said rotor is a permanent magnet rotor having a North pole layer and a South pole layer thereon mounted on a drive shaft, thereby to provide a two pole motor.

15. The instrument of claim 1 wherein said micro motor includes a cylindrical motor housing, said flexible circuit board being coiled into a cylinder within and adjacent the inner surface of said housing and having four flat stator coil branches interconnected with each other and mounted thereon.

16. The instrument of claim 15 wherein said four flat stator coil branches, before being folded into a cylinder, are formed from a sheet of conductive material mounted on the flexible circuit board.

17. The instrument of claim 16 wherein said sheet of material has an upper edge and a lower edge, said lower edge has a continuous margin forming a continuous conductor, and said sheet of material has four leads extending from the upper edge of said sheet of material.

18. The instrument of claim 17 wherein said sheet of material has three slots extending from the upper edge toward, but not to, the lower edge so as to separate said sheet of material into said four flat stator coil branches.

19. The instrument of claim 18 wherein each section of said sheet of material containing a stator coil branch has two internal, parallel spaced, notches therein parallel to the slots, thereby to form each coil branch with three legs integrally connected together by said integral lower margin of said sheet of material.

20. The instrument of claim 19 wherein said first and third coil branches form a first frame coil and are arranged to receive one phase of A.C. electrical current and the second and fourth coil branches form a second frame coil are arranged to receive a second phase of A.C. electrical current.

21. The instrument of claim 19 wherein each side leg of each coil branch has a current density which is 71% of the current density in the middle leg of each coil branch.

22. The instrument of claim 15 wherein said micro motor includes an end cap mounted to one end of the motor housing and has four slots therein through which four leads from said stator frame coils can extend for connection to conductors leading to two phase shifted current sources.

23. The instrument of claim 15 wherein said micro motor includes two spaced apart bearing members each having four spaced apart notches on the periphery thereof, the notches permitting passage of fluid into and through the stator housing and the notches in the bearing at one end of the stator housing providing a passageway for flat metal leads extending from the stator frame coils.

24. The instrument of claim 1 wherein said motor has a side which faces toward said distal end and includes drive shaft which extends from said side facing said distal end, said rotatable member is a rotatable acoustic mirror which is located in said distal end portion of said catheter and is connected to said drive shaft, said rotatable mirror has a mirror face that faces distally and that lies in a plane that intersects at an angle the axis of the drive shaft and the axis of the propagation of sound waves from said means for generating sound waves, and said means for generating sound waves comprises a transducer mounted in said tip at said distal end of said catheter.

25. The instrument of claim 1 wherein said flexible circuit board has at least two flat stator coil branches formed thereon to form at least one frame coil and wherein each coil branch is constructed and arranged to produce a current density profile of a sinusoidal nature in an arcuate direction along the circumference of the coiled circuit board.

26. A synchronous alternating current micro motor comprising a rotor and a stator having at least two flat stator branches mounted on a flexible circuit board which is coiled into a cylinder around said rotor.

27. A synchronous alternating current two phase micro motor comprising a rotor and a stator having four flat stator coil branches forming two frame coils, said coil branches being mounted on a flexible circuit board which is coiled into a cylinder around said rotor and said rotor being a permanent magnet rotor having a North pole layer and a South pole layer thereon mounted on a drive shaft, thereby to provide a two pole motor.

28. The motor of claim 27 including a cylindrical motor housing, said flexible circuit board being coiled into a cylinder within and adjacent the inner surface of said housing and having said four flat stator coil branches interconnected with each other and mounted thereon.

29. The motor of claim 28 wherein said sheet of material has an upper edge and a lower edge, said lower edge having a continuous margin forming a continuous conductor, and said sheet of material has four leads extending from the upper edge of said sheet of material.

30. The motor of claim 29 wherein each section of said sheet of material containing a stator coil branch has two internal, parallel spaced, notches therein parallel to the slots, thereby to form each coil branch with three legs integrally connected together by said integral lower margin of said sheet of material.

31. The motor of claim 27 wherein said four flat stator coil branches, before being folded into a cylinder, are formed from a sheet of conductive material mounted on the flexible circuit board.

32. The motor of claim 31 wherein said sheet of material has three slots extending from the upper edge toward, but not to, the lower edge so as to separate said sheet of material into four flat stator coil branches.

33. The motor of claim 32 wherein the first and third coil branches form a first frame coil and are arranged to receive one phase of A.C. electrical current and the second and fourth coil branches form a second frame coil and are arranged to receive a second phase of A.C. electrical current.

34. The motor of claim 32 wherein each side leg of each coil branch has a current density which is 71% of the current density in the middle leg of each coil branch.

35. The motor of claim 27 including an end cap mounted to one end of the motor housing and has four slots therein through which four leads from said stator frame coils can extend for connection to conductors leading to two phase shifted sources.

36. The motor of claim 27 including two spaced apart bearing members each having four spaced apart notches on the periphery thereof, the notches permitting passage of fluid into and through the stator housing and the notches in the bearing at one end of the stator housing providing a passageway for flat metal leads extending from the stator frame coils.

37. A synchronous alternating current micro motor comprising a rotor and a stator having at least two flat stator coil branches mounted on a flexible circuit board which is coiled into a cylinder around said rotor, said two flat stator coil branches being arranged to form at least one frame coil and each coil branch being constructed and arranged to produce a current density profile of a sinusoidal nature in an arcuate direction along the circumference of the coiled circuit board.

38. A disposable ultrasonic instrument for the examination of blood vessels or for the treatment of blood vessels or for the guiding of an interventional device through blood vessels and similar lumina having a small transverse cross-section, said instrument comprising a distal end portion and being adapted to being introduced into a lumen, said distal end portion having a diameter not greater than 3 millimeters, a rotatable member in said distal end portion, and a micro motor being positioned in said distal end portion and including flat stator coils mounted on at least one flexible circuit board which is coiled into a cylinder, and a rotor which is coupled to said rotatable member for rotating said rotatable member at a selected rpm, and said instrument further including means for generating and supplying sound waves to said rotatable member.

* * * * *

UNITED STATES PATENT AND TRADEMARK OFFICE
CERTIFICATE OF CORRECTION

PATENT NO. : 5,240,003
DATED : August 31, 1993
INVENTOR(S) : Charles T. Lancee; Nicholaas Bom It is certified that error appears in the above-indentified patent and that said Letters Patent is hereby corrected as shown below:

Column 2, line 45 "vessel like the" should be --vessel, nor is it intended to be inserted into a blood vessel like the--.

Column 3, line 9 "catheter holding" should be --catheter including--.

Column 4, line 8 "catheter" should be --catheter 1--.

Column 4, line 32 "by a motor" should be --by the motor--.

Column 7, line 50 "to assist the" should be --to assist in the--.

Column 14, line 15 "stator branches" should be --stator coil branches--.

Signed and Sealed this

Twelfth Day of July, 1994

Attest:

BRUCE LEHMAN

*Attesting Officer*     *Commissioner of Patents and Trademarks*